(12) United States Patent
Reese et al.

(10) Patent No.: US 8,434,346 B2
(45) Date of Patent: *May 7, 2013

(54) SYNTHETIC MATERIALS FOR PDC CUTTER TESTING OR FOR TESTING OTHER SUPERHARD MATERIALS

(75) Inventors: Michael R. Reese, Houston, TX (US); Federico Bellin, Pau (FR); Alfazazi Dourfaye, Paris (FR); Gary M. Thigpen, Houston, TX (US)

(73) Assignee: Varel Europe S.A.S., Pau (FR)

( * ) Notice: Subject to any disclaimer, the term of this patent is extended or adjusted under 35 U.S.C. 154(b) by 275 days.

This patent is subject to a terminal disclaimer.

(21) Appl. No.: 12/916,776

(22) Filed: Nov. 1, 2010

(65) Prior Publication Data

US 2011/0146372 A1   Jun. 23, 2011

Related U.S. Application Data

(60) Provisional application No. 61/288,143, filed on Dec. 18, 2009.

(51) Int. Cl.
*G01N 3/56* (2006.01)
(52) U.S. Cl.
USPC ................................................. 73/7
(58) Field of Classification Search ............... 73/7, 104, 73/105, 866; 175/327, 434
See application file for complete search history.

(56) References Cited

U.S. PATENT DOCUMENTS

| 6,238,448 | B1 | 5/2001 | Rouse et al. | |
|---|---|---|---|---|
| 6,328,644 | B1 | 12/2001 | Kuramochi et al. | |
| 7,558,369 | B1 | 7/2009 | Mourik et al. | |
| 2008/0178535 | A1* | 7/2008 | Wan | 51/297 |
| 2011/0146373 | A1* | 6/2011 | Reese et al. | 73/7 |
| 2011/0146374 | A1* | 6/2011 | Reese et al. | 73/7 |

FOREIGN PATENT DOCUMENTS

WO         96/23952        8/1996

* cited by examiner

*Primary Examiner* — John Fitzgerald
*Assistant Examiner* — David Z Huang
(74) *Attorney, Agent, or Firm* — King & Spalding LLP

(57) ABSTRACT

A target cylinder and a method for testing a superhard component thereon. The target cylinder includes a first end, a second end, and a sidewall extending from the first end to the second end. At least one of the second end and the sidewall is an exposed portion that makes contact with the superhard component to determine at least one property of the superhard component. The exposed portion comprises at least one synthetic material having at least one of a compressive strength raging from about 12 kpsi to about 30 kpsi, an abrasiveness ranging from about 1 Cerchars to about 6 Cerchars, and an iron content ranging from about 5 percent to about 10 percent. Optionally, the exposed portion further comprises a second material interveningly positioned between or within the synthetic material in a predetermined and repeatable pattern.

34 Claims, 5 Drawing Sheets

SYNTHETIC MATERIALS FOR PDC CUTTER TESTING OR FOR TESTING OTHER SUPERHARD MATERIALS

CROSS-REFERENCE TO RELATED APPLICATIONS

This application claims priority to U.S. Provisional Patent Application No. 61/288,143, entitled "Method and Apparatus for Testing Superhard Material Performance," filed Dec. 18, 2009, the entirety of which is incorporated by reference herein.

The present application is related to U.S. patent application Ser. No. 12/916,815, entitled "Synthetic Materials for PDC Cutter Testing or for Testing other Superhard Materials" and filed on Nov. 1, 2010, and U.S. patent application Ser. No. 12/916,847, entitled "Synthetic Materials for PDC Cutter Testing or for Testing other Superhard Materials" and filed on Nov. 1, 2010, the disclosures of which are incorporated herein by reference.

TECHNICAL FIELD

The present invention relates generally to a method and apparatus for testing PDC cutters or other superhard components; and more particularly, to a method and apparatus for testing the abrasive wear resistance and/or the impact resistance of PDC cutters or other superhard components.

BACKGROUND

FIG. 1 shows a superhard component 100 that is insertable within a downhole tool (not shown) in accordance with an exemplary embodiment of the invention. One example of a superhard component 100 is a cutting element 100, or cutter, for rock bits. The cutting element 100 typically includes a substrate 110 having a contact face 115 and a cutting table 120. The cutting table 120 is fabricated using an ultra hard layer which is bonded to the contact face 115 by a sintering process. The substrate 110 is generally made from tungsten carbide-cobalt, or tungsten carbide, while the cutting table 120 is formed using a polycrystalline ultra hard material layer, such as polycrystalline diamond ("PCD"), polycrystalline cubic boron nitride ("PCBN"), or tungsten carbide mixed with diamond crystals (impregnated segments). These cutting elements 100 are fabricated according to processes and materials known to persons having ordinary skill in the art. The cutting element 100 is referred to as a polycrystalline diamond compact ("PDC") cutter when PCD is used to form the cutting table 120. PDC cutters are known for their toughness and durability, which allow them to be an effective cutting insert in demanding applications. Although one type of superhard component 100 has been described, other types of superhard components 100 can be utilized.

Common problems associated with these cutters 100 include chipping, spalling, partial fracturing, cracking, and/or flaking of the cutting table 120. These problems result in the early failure of the cutting table 120. Typically, high magnitude stresses generated on the cutting table 120 at the region where the cutting table 120 makes contact with earthen formations during drilling can cause these problems. These problems increase the cost of drilling due to costs associated with repair, production downtime, and labor costs. For these reasons, testing methods have been developed to ascertain the abrasion resistance and/or impact resistance of cutters 100 so that improved cutter longevity is achieved and the problems mentioned above are substantially reduced.

Superhard components 100, which include PDC cutters 100, have been tested for abrasive wear resistance through the use of two conventional testing methods. Early in the development of PDC materials, the abrasive wear resistance was tested using a conventional granite log test, which is described in further detail with respect to FIG. 2. However, as the PDC cutters 100 became more wear resistant and too much time and conventional target cylinders 250 (FIG. 2) were required to complete the conventional granite log test, the conventional vertical turret lathe ("VTL") test, which is described in further detail with respect to FIG. 3, replaced the conventional granite log test for testing abrasive wear resistance.

FIG. 2 shows a lathe 200 for testing abrasive wear resistance of a superhard component 100 using a conventional granite log test. Although one exemplary apparatus configuration for the lathe 200 is provided, other apparatus configurations can be used without departing from the scope and spirit of the exemplary embodiment. Referring to FIG. 2, the lathe 200 includes a chuck 210, a tailstock 220, and a tool post 230 positioned between the chuck 210 and the tailstock 220. A conventional target cylinder 250 has a first end 252, a second end 254, and a sidewall 258 extending from the first end 252 to the second end 254. According to the conventional granite log test, sidewall 258 is an exposed surface 259 which makes contact with the superhard component 100 during the test. The first end 252 is coupled to the chuck 210, while the second end 254 is coupled to the tailstock 220. The chuck 210 is configured to rotate, thereby causing the conventional target cylinder 250 to also rotate along a central axis 256 of the conventional target cylinder 250. The tailstock 220 is configured to hold the second end 254 in place while the conventional target cylinder 250 rotates. The conventional target cylinder 250 is fabricated from a single uniform material, which is typically a natural rock type, such as granite, or concrete. Other single uniform rock types have been used for the conventional target cylinder 250, which includes, but is not limited to, Jackfork sandstone, Indiana limestone, Berea sandstone, Carthage marble, Champlain black marble, Berkley granite, Sierra white granite, Texas pink granite, and Georgia gray granite. The conventional target cylinder 250 has a compressive strength of about 25,000 pounds per square inch ("psi") or less and an abrasiveness of about 6 CAI or less when natural rock types are used. These conventional target cylinders 250 fabricated from natural rock types are costly to acquire, shape, ship, and handle. The conventional target cylinder 250 has a compressive strength of about 12,000 psi or less and an abrasiveness of about 2 CAI or less when concrete is used.

The PDC cutter 100 is fitted to the lathe's tool post 230 so that the PDC cutter's cutting table 120 makes contact with the conventional target cylinder's exposed surface 259 and drawn back and forth across the exposed surface 259. The tool post 230 has an inward feed rate on the conventional target cylinder 250. The abrasive wear resistance for the PDC cutter 100 is determined as a wear ratio, which is defined as the volume of conventional target cylinder 250 that is removed to the volume of the PDC cutter's cutting table 120 that is removed. This wear ratio can be referred to as a grinding ratio ("G-Ratio"). Common values of the G-Ratio range from about 1,000,000/1 to 15,000,000/1 depending on the abrasiveness of the conventional target cylinder and the PDC cutter. Alternatively, instead of measuring volume of rock removed, the distance that the PDC cutter 100 travels across the conventional target cylinder 250 can be measured and used to quantify the abrasive wear resistance for the PDC cutter 100. Common values of the travelling distance range from about 15,000 feet to about 160,000 feet depending on the abrasiveness of the conventional target cylinder and the PDC cutter. Alternatively, other methods known to persons having ordinary skill in the art can be used to determine the wear resistance using the conventional granite log test. Operation and construction of the lathe 200 is known to people having ordinary skill in the art. Descriptions of this type of test is found in the Eaton, B. A., Bower, Jr., A. B., and Martis, J. A. "Manufactured Diamond Cutters Used In Drilling Bits." *Journal of Petroleum Technology*, May 1975, 543-551. Society of Petroleum Engineers paper 5074-PA, which was published in the Journal of Petroleum Technology in May 1975, and also found in Maurer, William C., *Advanced Drilling Techniques*, Chapter 22, The Petroleum Publishing Company, 1980, pp. 541-591, which is incorporated by reference herein.

As previously mentioned, this conventional granite log test was adequate during the initial stages of PDC cutter 100 development. However, PDC cutters 100 have become more resistant to abrasive wear as the technology for PDC cutters 100 improved. Current technology PDC cutters 100 are capable of cutting through many conventional target cylinders 250 without ever developing any appreciable and measurable wear flat; thereby, making the conventional granite log test method inefficient and too costly for measuring the abrasive wear resistance of superhard components 100.

FIG. 3 shows a vertical turret lathe 300 for testing abrasive wear resistance of a superhard component 100 using a conventional vertical turret lathe ("VTL") test. Although one exemplary apparatus configuration for the VTL 300 is provided, other apparatus configurations can be used without departing from the scope and spirit of the exemplary embodiment. The vertical turret lathe 300 includes a rotating table 310 and a tool holder 320 positioned above the rotating table 310. A conventional target cylinder 350 has a first end 352, a second end 354, and a sidewall 358 extending from the first end 352 to the second end 354. According to the conventional VTL test, second end 354 is an exposed surface 359 which makes contact with a superhard component's cutting table 120 during the test. The conventional target cylinder 350 is typically about thirty inches to about sixty inches in diameter, but can be smaller or larger depending upon the testing requirements. The conventional target cylinder 350 is typically larger in diameter than the conventional target cylinder 250 (FIG. 2).

The first end 352 is mounted on the lower rotating table 310 of the VTL 300, thereby having the exposed surface 359 face the tool holder 320. The PDC cutter 100 is mounted in the tool holder 320 above the conventional target cylinder's exposed surface 359 and makes contact with the exposed surface 359. The conventional target cylinder 350 is rotated via the rotating table 310 as the tool holder 320 cycles the PDC cutter 100 from the center of the conventional target cylinder's exposed surface 359 out to its edge and back again to the center of the conventional target cylinder's exposed surface 359. The tool holder 320 has a predetermined downward feed rate.

The VTL 300 is generally a larger machine when compared to the lathe 200 (FIG. 2) used for the conventional granite log test. The conventional VTL test allows for larger depths of cut to be made in the conventional target cylinder 350 and for the use of a larger conventional target cylinder 350 when compared to the depths of cut made and the size of the conventional target cylinder 250 (FIG. 2) used in the conventional granite log test. The capability of having larger depths of cut allows for higher loads to be placed on the PDC cutter 100. Additionally, the larger conventional target cylinder 350 provides for a greater rock volume for the PDC cutter 100 to act on and hence a longer duration for conducting the test on the same conventional target cylinder 350. Thus, fewer conventional target cylinders 350 are used when performing the conventional VTL test when compared to the number of conventional target cylinders 250 (FIG. 2) that are used in the conventional granite log test. The conventional target cylinder 350 is typically fabricated entirely from granite; however, the conventional target cylinder can be fabricated entirely from another single uniform natural material that includes, but is not limited to, Jackfork sandstone, Indiana limestone, Berea sandstone, Carthage marble, Champlain black marble, Berkley granite, Sierra white granite, Texas pink granite, and Georgia gray granite, or concrete. The conventional target cylinder 350 has a compressive strength of about 25,000 psi or less and an abrasiveness of about 6 CAI or less when natural rock types are used. As previously mentioned, these conventional target cylinders 350 fabricated from natural rock types are costly to acquire, shape, ship, and handle. The conventional target cylinder 350 has a compressive strength of about 12,000 psi or less and an abrasiveness of about 2 CAI or less when concrete is used. The abrasive wear resistance for the PDC cutter 100 is determined as a wear ratio, which is defined as the volume of conventional target cylinder 350 that is removed to the volume of the PDC cutter 100 that is removed. This wear ratio can be referred to as a grinding ratio ("G-Ratio"). Common values of the G-Ratio range from about 1,000,000/1 to about 15,000,000/1 depending on the abrasiveness of the conventional target cylinder and the PDC cutter. Alternatively, instead of measuring volume of rock removed, the distance that the PDC cutter 100 travels across the conventional target cylinder 350 can be measured and used to quantify the abrasive wear resistance for the PDC cutter 100. Common values of the travelling distance range from about 15,000 feet to about 160,000 feet depending one the abrasiveness of the conventional target cylinder and the PDC cutter.

Referring back to FIGS. 2 and 3, the conventional target cylinders 250 and 350 have limitations due to the material compositions used in fabricating the conventional target cylinders 250 and 350, which is either a natural material or concrete. When using a natural material, the material must be mined and shaped before the natural material becomes suitable for use as a conventional target cylinder 250 and 350. Additionally, certain provisions are to be made when using these natural materials due to their variability in properties. For instance, once a natural material is selected for use as the conventional target cylinder 250 and 350, additional natural material must be selected from the same mine to avoid expensive recalibration of the test. The same natural material from a different mine is likely to have different properties and thus result in testing discrepancies. Further, shipping costs, limited supplies of natural material, and natural variations all increase the cost and ability to obtain repeatable test results.

Concrete, however, has some advantages over natural material when fabricating the conventional target cylinders 250 and 350. Concrete is widely available and relatively inexpensive when compared to natural materials. Concrete is fabricated using local materials hence reducing transportation costs. Although concrete has some advantages over natural materials, concrete also has several disadvantages. According to one disadvantage, concrete has a much lower compressive strength when compared to rock strength found in the field. Conventional concrete has a typical compressive strength of about three kilo-pounds per square inch ("kpsi"), while some specialty concretes can reach about twelve to kpsi. However, rock strength found in the field typically ranges in compressive strength from about twenty kpsi to about sixty kpsi. Thus, the tests performed using concrete-formed conventional target cylinders 250 and 350 are not indicative of field results. According to another disadvantage, fabricating concrete is a much longer time consuming process. Concrete is typically cured for about twenty-eight days so that its specified strength is reliably reached. As known to people having ordinary skill in the art, a long fabrication duration for preparing the conventional target cylinder 250 and 350 becomes very expensive due to loss of time.

BRIEF DESCRIPTION OF THE DRAWINGS

The foregoing and other features and aspects of the invention are best understood with reference to the following description of certain exemplary embodiments, when read in conjunction with the accompanying drawings, wherein.

The drawings illustrate only exemplary embodiments of the invention and are therefore not to be considered limiting of its scope, as the invention may admit to other equally effective embodiments.

BRIEF DESCRIPTION OF EXEMPLARY EMBODIMENTS

The present invention is directed to a method and apparatus for testing the abrasive wear resistance and/or the impact resistance of superhard components. Although the description of exemplary embodiments is provided below in conjunction with a PDC cutter, alternate embodiments of the invention may be applicable to other types of superhard components including, but not limited to, PCBN cutter or other superhard components known or not yet known to persons having ordinary skill in the art.

Figure 4:
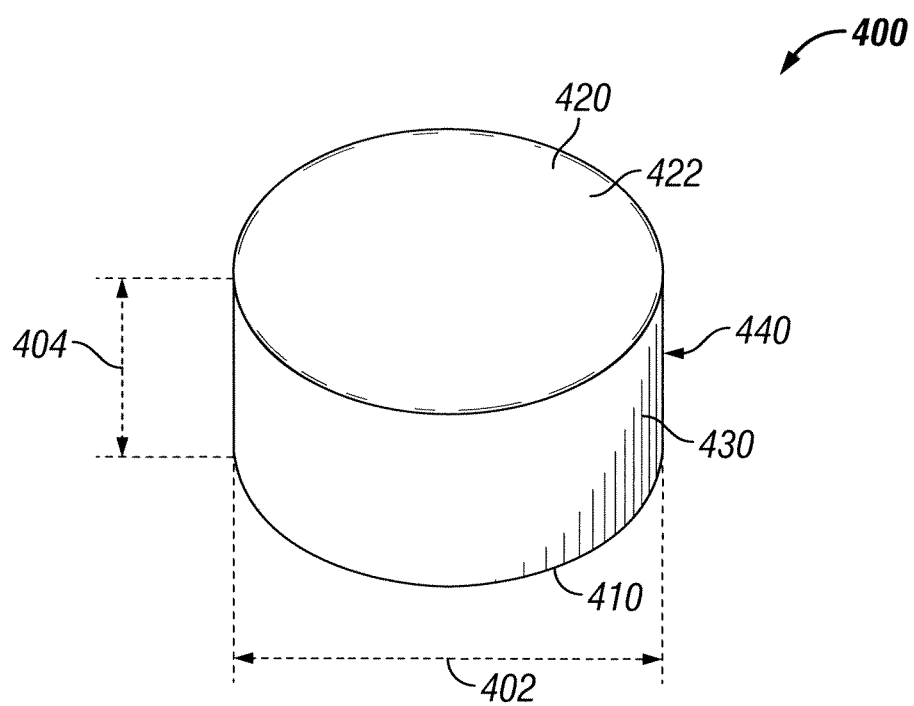
FIG. 4 shows a top perspective view of a target cylinder in accordance with an exemplary embodiment of the invention.

The invention is better understood by reading the following description of non-limiting, exemplary embodiments with reference to the attached drawings, wherein like parts of each of the figures are identified by like reference characters, and which are briefly described as follows. FIG. 4 shows a top perspective view of a target cylinder 400 in accordance with an exemplary embodiment of the invention. Referring to FIG. 4, the target cylinder 400 is cylindrically shaped and includes a first end 410, a second end 420, and a sidewall 430 extending from the first end 410 to the second end 420. According to this exemplary embodiment, the second end 420 is also referred to as an exposed portion 422 of the target cylinder 400 because the second end 420 is subjected to contact with the superhard component 100 (FIG. 1) when the testing is performed using the VTL test. The exposed portion 422 is substantially planar. Although the target cylinder 400 is cylindrically shaped, the target cylinder 400 can be any other geometric or non-geometric shape without departing from the scope and spirit of the exemplary embodiment. The target cylinder 400 has a diameter 402 of approximately three feet and a height 404 of approximately four inches. However, in alternate exemplary embodiments, the diameter 402 can range from about four inches to about ten feet without departing from the scope and spirit of the exemplary embodiment. Additionally, in alternate exemplary embodiments, the height 404 can range from about one inch to about twenty feet without departing from the scope and spirit of the exemplary embodiment. Although the target cylinder 400 is dimensioned for use in the conventional VTL test, the target cylinder 400 can be dimensioned for use in the conventional granite log test, as previously described above.

Figure 5:
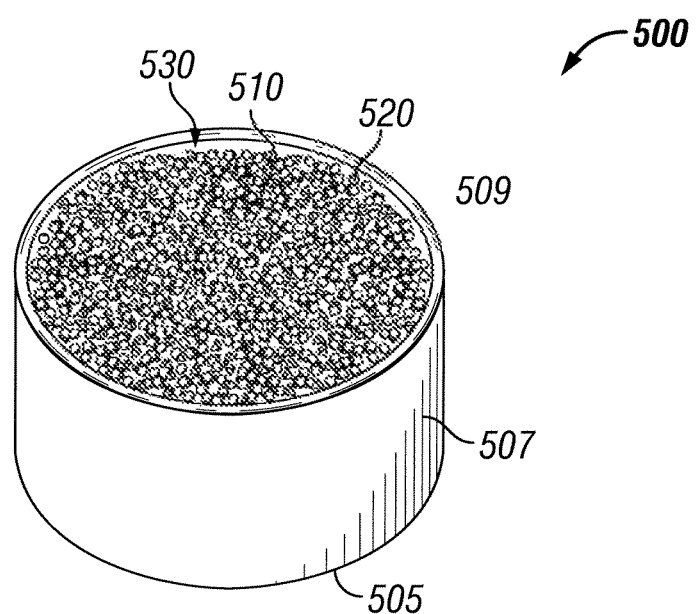
FIG. 5 shows a top perspective view of a casting form used for forming the target cylinder of FIG. 4 according to an exemplary embodiment of the invention.

The target cylinder 400 is fabricated using a synthetic material 440. FIG. 5 shows a top perspective view of a casting form 500 used for forming the target cylinder 400 according to an exemplary embodiment of the invention. Referring to FIG. 5, the casting form 500 includes a base 505 and a sidewall 507 extending substantially perpendicular from the base 505. The base 505 and the sidewall 507 collectively form a cavity 509 therein. The cavity is shaped into a negative shape of the target cylinder 400 (FIG. 4), which is a cylindrical shape. However, the cavity 509 is shaped into other shapes including, but not limited to, the negative shapes of a wheel for use on a grinding wheel (not shown), or other geometric or non-geometric forms according to other exemplary embodiments. Thus, in other exemplary embodiments, the target cylinder 400 (FIG. 4) can be dimensioned and shaped into a wheel for use in a grinding wheel, a square-shaped cylinder, an oval-shaped cylinder, a triangular-shaped cylinder, or any other shape. The cavity 509 is filled with the aggregate material 510 and the cementing agent 520, and thereafter processed, according to methods known to people having ordinary skill in the art and which is briefly described below, to convert the aggregate material 510 and the cementing agent 520 into the synthetic material 440 (FIG. 4). The synthetic material 440 (FIG. 4) is formed from the aggregate material 510 and the cementing agent 520, which bonds the aggregate material 510 to one another.

Referring to FIGS. 4 and 5, according to some exemplary embodiments, the cementing agent 520 is mixed together with the aggregate material 510, placed into the casting form 500, and processed to form the resulting synthetic material 440. According to other exemplary embodiments, the cementing agent 520 is coated onto and/or around the aggregate material 510, placed into the casting form 500, and processed to form the resulting synthetic material 440. After the synthetic material 440 is formed, the casting form 500 is removed. Once the casting form 500 is removed, the exposed portion 422 is made smooth and substantially planar. According to some exemplary embodiments, the casting form 500 is destroyed, while in other exemplary embodiments, the casting form 500 is removable and reusable.

The aggregate material 510 includes, but is not limited to, blast media and foundry casting media. Blast media includes, but is not limited to, silica sand, garnet, silicon carbide, aluminum oxide, zircon sand, and other blast media types known to people having ordinary skill in the art. These aggregate materials 510 are widely available for industrial applications and have controlled hardness and particle size. The cementing agent 520 includes, but is not limited to, sodium silicate which is also referred to as water glass, a plastic resin, a multi-part epoxy resin, clay based ceramic particles for forming ceramic bonds within the resulting synthetic material 440, known compounds for producing a vitrified bond within the resulting synthetic material 440, and an abrasive cement. According to some exemplary embodiments, the cementing agent 520 is a strong and fast curing material, wherein the curing time ranges from almost instantly to up to about five days. In other exemplary embodiments, the curing time can range from almost instantly to about fifteen days. By using cementing agents 520 that are strong and fast curing, synthetic materials 440 are fabricated with a controlled compressive strength and with the required efficiency. Alternatively, the synthetic material 440 is fabricated using other synthetic manufactured materials, such as Corian®, Zodiaq®, Silestone®, Ceracem®, Sikacrete®, Condensil®, and aluminum oxide according to some exemplary embodiments. According to some exemplary embodiments, the other synthetic manufactured materials form the synthetic material 440 by laminating slabs of these other synthetic manufactured materials together and shaping them into a desired shape.

According to one example, the synthetic material 440 is produced by mixing the aggregate material 510, for example silica sand, with sodium silicate to form a mixture 530. The sodium silicate is coated onto the aggregate material 510 according to some exemplary embodiments. The mixture 530 is packed into the cavity 509 of the casting form 500, which has a predetermined shape. The predetermined shape is a negative shape of the target cylinder 400 that is to be formed. However, as previously mentioned, the cavity 509 has a negative shape of a wheel (not shown) that, once formed, the wheel can be used in a traditional grinding wheel apparatus (not shown) according to some other exemplary embodiments. The mixture 530 is then cured by applying carbon dioxide to the mixture 530. During the curing process, the mixture 530 is solidified to form the synthetic material 440 in the negative shape of the cavity 509. The curing process occurs in less than about an hour; however, the length of time can be greater or less in other exemplary embodiments. The following chemical reaction takes place during the curing process:

$$Na_2SiO_3 + CO_2 \rightarrow Na_2CO_3 + SiO_2$$

Based upon the reaction provided above, the sodium silicate forms a silicon oxide during the curing reaction while also facilitates bonding the aggregate material 510 to one another. Silicon oxide is the most abrasive component of sedimentary rocks. The silicon oxide content is increased as the reaction proceeds forward, thereby increasing the abrasiveness of the resulting synthetic material 440. According to some exemplary embodiments, the reaction occurs at about room temperature and at about atmospheric pressure; however, the temperature and/or the pressure can be altered in different exemplary embodiments.

According to another example, the synthetic material 440 is produced by mixing the aggregate material 510, for example silicon oxide, with plastic resin to form a mixture 530. The plastic resin is coated onto the aggregate material 510 according to some exemplary embodiments. The mixture 530 is packed into the cavity 509 of the casting form 500, which has a predetermined shape. The predetermined shape is a negative shape of the target cylinder 400 that is to be formed. However, as previously mentioned, the cavity 509 has a negative shape of a wheel (not shown) that, once formed, the wheel can be used in a traditional grinding wheel apparatus (not shown) according to some other exemplary embodiments. The casting form 500, along with the mixture 530, is then placed in an oven (not shown) where the mixture 530 is cured at a proper temperature. According to some exemplary embodiments, the proper temperature ranges from about 200° F. to about 300° F.; however, the temperature can be higher or lower in other exemplary embodiments. When subjected to the proper temperature, the plastic resin melts and bonds the aggregate material 510 together into a single piece which forms the negative shape of the cavity 509. The curing process occurs in about two hours; however, the length of time can be greater or less in other exemplary embodiments. According to some exemplary embodiments, the process occurs at about atmospheric pressure; however, the pressure can be altered in different exemplary embodiments.

According to another example, the synthetic material 440 is produced by mixing the aggregate material 510, for example silica sand, with a multi-part epoxy resin to form a mixture 530. The multi-part epoxy resin typically consists of two parts, an epoxy resin and a hardener, which when placed in contact with one another initiates a reaction which bonds the aggregate material 510 together. According to one example, the multi-part epoxy resin includes phenolic resin and hexamine catalyst. In some exemplary embodiments, the multi-part epoxy resin includes more than two parts. The mixture 530 is packed into the cavity 509 of the casting form 500, which has a predetermined shape. The predetermined shape is a negative shape of the target cylinder 400 that is to be formed. However, as previously mentioned, the cavity 509 has a negative shape of a wheel (not shown) that, once formed, the wheel can be used in a traditional grinding wheel apparatus (not shown) according to some other exemplary embodiments. Within the casting form 500, the reaction occurs when each of the components of the multi-part epoxy resin contact one another; thereby resulting in bonding the aggregate material 510 together to form a single piece which forms the negative shape of the cavity 509. The curing process occurs in about five hours; however, the length of time can be greater or less in other exemplary embodiments. According to some exemplary embodiments, the process occurs at a temperature ranging between about 70° F. and 480° F. and at a pressure that is about one atmosphere; however, the temperature and/or the pressure can be altered in different exemplary embodiments.

According to another example, the synthetic material 440 is produced by mixing the aggregate material 510, for example silica sand mixed with a mineral belonging to the phyllosilicates group, with sodium silicate to form a mixture 530. The sodium silicate is coated onto the aggregate material 510 according to some exemplary embodiments. The mixture 530 is packed into the cavity 509 of the casting form 500, which has a predetermined shape. The predetermined shape is a negative shape of the target cylinder 400 that is to be formed. However, as previously mentioned, the cavity 509 has a negative shape of a wheel (not shown) that, once formed, the wheel can be used in a traditional grinding wheel apparatus (not shown) according to some other exemplary embodiments. The mixture 530 is then cured by applying carbon dioxide to the mixture and increasing the temperature to about 1600° F. During the curing process, the mixture 530 is solidified to form the synthetic material 440 in the negative shape of the cavity 509. The curing process occurs in about 9 hours; however, the length of time can be greater or less in other exemplary embodiments. The following chemical reaction takes place during the curing process:

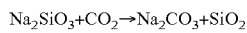

Based upon the reaction provided above, the sodium silicate forms a silicon oxide during the curing reaction while also facilitates bonding the aggregate material 510 to one another. Silicon oxide is the most abrasive component of sedimentary rocks. The silicon oxide content is increased as the reaction proceeds forward, thereby increasing the abrasiveness of the resulting synthetic material 440. According to some exemplary embodiments, the reaction occurs at about room temperature and at about ten psi to about fifteen psi pressure; however, the temperature and/or the pressure can be altered in different exemplary embodiments.

According to another example, the synthetic material 440 is produced by mixing the aggregate material 510, for example silica sand, with clay based ceramic material to form a mixture 530. However, other types of ceramic material are used in other exemplary embodiments. The mixture 530 is packed into the cavity 509 of the casting form 500, which has a predetermined shape. The predetermined shape is a negative shape of the target cylinder 400 that is to be formed. However, as previously mentioned, the cavity 509 has a negative shape of a wheel (not shown) that, once formed, the wheel can be used in a traditional grinding wheel apparatus (not shown) according to some other exemplary embodiments. The casting form 500, along with the mixture 530, is then placed in a furnace (not shown) and then fired where the mixture 530 is cured and ceramic bonds are formed. According to some exemplary embodiments, the temperature ranges from about 1745° F. to about 2012° F.; however, the temperature can be altered in other exemplary embodiments. When fired, ceramic bonds are formed and the aggregate material 510 bonds together into a single piece which forms the negative shape of the cavity 509. The firing process occurs in about four to about six hours; however, the length of time can be greater or less in other exemplary embodiments. According to some exemplary embodiments, the process occurs at about room pressure; however, the pressure can be altered in different exemplary embodiments.

According to another example, the synthetic material 440 is produced by mixing the aggregate material 510, for example Condensil®, with an abrasive cement, for example Ceracem®, to form a mixture 530. The Condensil® is formed from sand and is used as a component for high performance concrete. In certain exemplary embodiments, the Condensil® includes about 95% silicon oxide; however, the percent of silicon dioxide is variable in other exemplary embodiments. In certain exemplary embodiments, the Condensil® includes a minimum of about 92% silicon oxide. According to some exemplary embodiments which use Condensil® and Ceracem®, the mixture 530 is used to obtain a high strength, high abrasivity concrete. The mixture 530 is packed into the cavity 509 of the casting form 500, which has a predetermined shape. The predetermined shape is a negative shape of the target cylinder 400 that is to be formed. However, as previously mentioned, the cavity 509 has a negative shape of a wheel (not shown) that, once formed, the wheel can be used in a traditional grinding wheel apparatus (not shown) according to some other exemplary embodiments. The mixture 530 is then cured to form a single piece which forms the negative shape of the cavity 509. According to some exemplary embodiments, the curing process is performed at about room temperature and at about atmospheric pressure; however, the temperature and/or the pressure is altered in other exemplary embodiments. The curing process occurs in about 7 days; however, the length of time can be greater or less in other exemplary embodiments. As greater proportions of Condensil® are used, the synthetic material 440 exhibits increased abrasivity. Conversely, as greater proportions of Ceracem® are used, the synthetic material 440 exhibits increased compressive strength. The proportions of each of aggregate material 510 and the abrasive cement can be varied to alter the properties of the synthetic material 440 in accordance with testing desires.

Although some examples have been provided above for fabricating the synthetic material 440 and facilitating the bonding of the aggregate material 510, the bonding methods include, but are not limited to, forming vitrified bonds, forming resinoid bonds, forming silicate bonds, forming shellac bonds, forming rubber bonds, and forming oxychloride bonds.

The resulting target cylinder 400 has an unconfined compressive strength of at least 18,000 psi. In certain exemplary embodiments, the resulting target cylinder 400 has an unconfined compressive strength ranging from about 18,000 psi to about 30,000 psi. In certain exemplary embodiments, the resulting target cylinder 400 has an unconfined compressive strength ranging from about 20,000 psi to about 28,000 psi. In certain exemplary embodiments, the resulting target cylinder 400 has an unconfined compressive strength ranging from about 22,000 psi to about 25,000 psi.

The resulting target cylinder 400 has an abrasiveness of at least 1.0 CAI when categorized pursuant to a Cerchar test. In certain exemplary embodiments, the resulting target cylinder 400 has an abrasiveness ranging from about one CAI to about two CAI when categorized pursuant to a Cerchar test. In certain exemplary embodiments, the resulting target cylinder 400 has an abrasiveness ranging from about two CAI to about four CAI when categorized pursuant to a Cerchar test. In certain exemplary embodiments, the resulting target cylinder 400 has an abrasiveness ranging from about four CAI to about six CAI when categorized pursuant to a Cerchar test.

Figure 1:
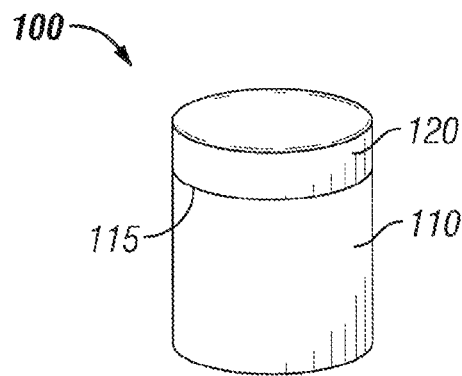
FIG. 1 shows a superhard component that is insertable within a downhole tool in accordance with an exemplary embodiment of the invention.

According to some exemplary embodiments, iron and/or iron alloys are included within the composition of the synthetic material 440 which forms the target cylinder 400. Iron in the form of cast iron particulates is included within the composition of the synthetic material 440 according to some exemplary embodiments. In another exemplary embodiment, iron in the form of steel buckshot is included within the composition of the synthetic material 440. Although some examples have been provided for the forms of iron that can be included within the synthetic material 440, other forms of iron can be included in the composition of the synthetic material 440 according to other exemplary embodiments. Iron and/or iron alloys are included within the composition of the synthetic material 440 for purposes of accelerating the wear rate of the cutting table 120 (FIG. 1) and accelerating the testing duration. Iron reacts with diamond and therefore is able to accelerate the wear rate of the cutting table 120 (FIG. 1).

According to some exemplary embodiments, Silicate alloys are included within the composition of the synthetic material 440 which forms the target cylinder 400. Silicon Oxide in the form of Condensil® is included within the composition of the synthetic material 440 according to some exemplary embodiments. Silicon Oxide alloys are included within the composition of the synthetic material 440 for purposes of increasing the abrasiveness and accelerating the wear rate of the cutting table 120 (FIG. 1) and accelerating the testing duration.

In certain exemplary embodiments, the content of Condensil® varies from about zero percent to about fifty percent of the weight of cement. In certain exemplary embodiments, the content of Condensil® varies from about five percent to about twenty-five percent of the weight of cement. In certain exemplary embodiments, the content of Condensil® varies from about five percent to about ten percent of the weight of cement.

According to some exemplary embodiments, iron composes about five percent to about ten percent of the total composition of the synthetic material 440; however the iron content is higher or lower according to other exemplary embodiments. In the exemplary embodiments where iron is included to form the synthetic material 440, the unconfined compressive strength of the target cylinder 400 is at least 12,000 psi. In certain exemplary embodiments where iron is included to form the synthetic material 440, the unconfined compressive strength of the target cylinder 400 ranges from about 12,000 psi to about 30,000 psi. In certain exemplary embodiments where iron is included to form the synthetic material 440, the unconfined compressive strength of the target cylinder 400 ranges from about 18,000 psi to about 25,000 psi. In certain exemplary embodiments where iron is included to form the synthetic material 440, the unconfined compressive strength of the target cylinder 400 ranges from about 22,000 psi to about 25,000 psi. In the exemplary embodiments where iron is included to form the synthetic material 440, the abrasiveness of the target cylinder 400 is at least one CAI when categorized pursuant to a Cerchar test. In certain exemplary embodiments where iron is included to form the synthetic material 440, the abrasiveness of the target cylinder 400 ranges from about 2 CAI to about 4 CAI when categorized pursuant to a Cerchar test. In certain exemplary embodiments where iron is included to form the synthetic material 440, the abrasiveness of the target cylinder 400 ranges from about 4 CAI to about 6 CAI when categorized pursuant to a Cerchar test. In certain exemplary embodiments where iron is included to form the synthetic material 440, the abrasiveness of the target cylinder 400 ranges from about 1 CAI to about 6 CAI when categorized pursuant to a Cerchar test.

The fabrication of the target cylinder 400 is repeatable so that an initially formed target cylinder 400 is substantially similar and has similar properties, such as unconfined compressive strength, abrasiveness, and composition, to a subsequently formed target cylinder 400. Once target cylinder 400 is formed, the target cylinder 400 can be used in the VTL test as described above. The target cylinder's first end 410 is coupled to the rotating table 310 (FIG. 3), thereby positioning the exposed portion 422 adjacent the tool holder 320 (FIG. 3) that has the cutter 100 (FIG. 3) mounted therein. Upon performing the VTL test using target cylinder 400, the abrasive wear resistance and/or the impact resistance for the PDC cutter 100 (FIG. 3) can be determined.

Figure 3:
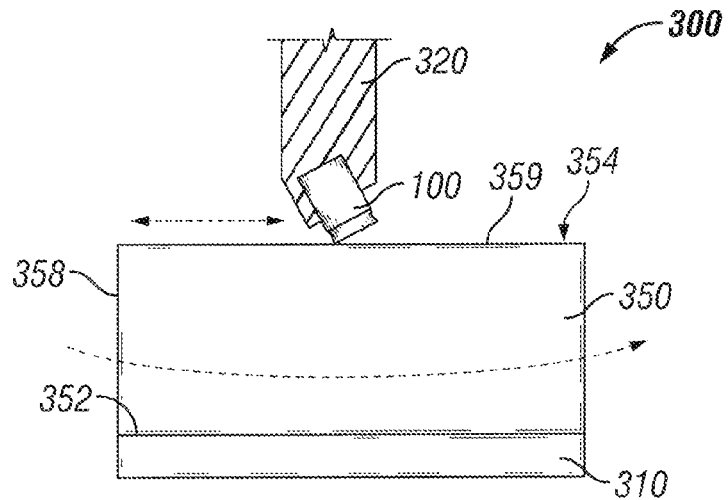
FIG. 3 shows a vertical turret lathe for testing abrasive wear resistance of a superhard component using a conventional vertical turret lathe test.

The abrasive wear resistance is determined as a wear ratio, which is defined as the volume of target cylinder 400 that is removed to the volume of the PDC cutter 100 (FIG. 3) that is removed. Alternatively, instead of measuring volume, the distance that the PDC cutter 100 (FIG. 3) travels across the target cylinder 400 can be measured and used to quantify the abrasive wear resistance for the PDC cutter 100 (FIG. 3). Alternatively, other methods known to persons having ordinary skill in the art can be used to determine the wear resistance using the VTL test.

The target cylinder 400 is able to test for abrasive wear resistance of cutters 100 (FIG. 1) with a minimum consumption of time, target material, and test cutters. The target cylinder 400 is formed having at least one of a higher unconfined compressive strength, a higher abrasiveness, and/or an inclusion of iron and/or iron alloy when compared to prior art conventional target cylinders. The target cylinder 400 can be made according to the same construction each time giving the test repeatability and continuity over the testing of numerous different cutter types.

According to some exemplary embodiments, the fabrication of the synthetic material 440 is performed in a press (not shown). This process facilitates fabrication of the synthetic material 440 so that the synthetic material 440 has a higher compressive strength.

Figure 6:
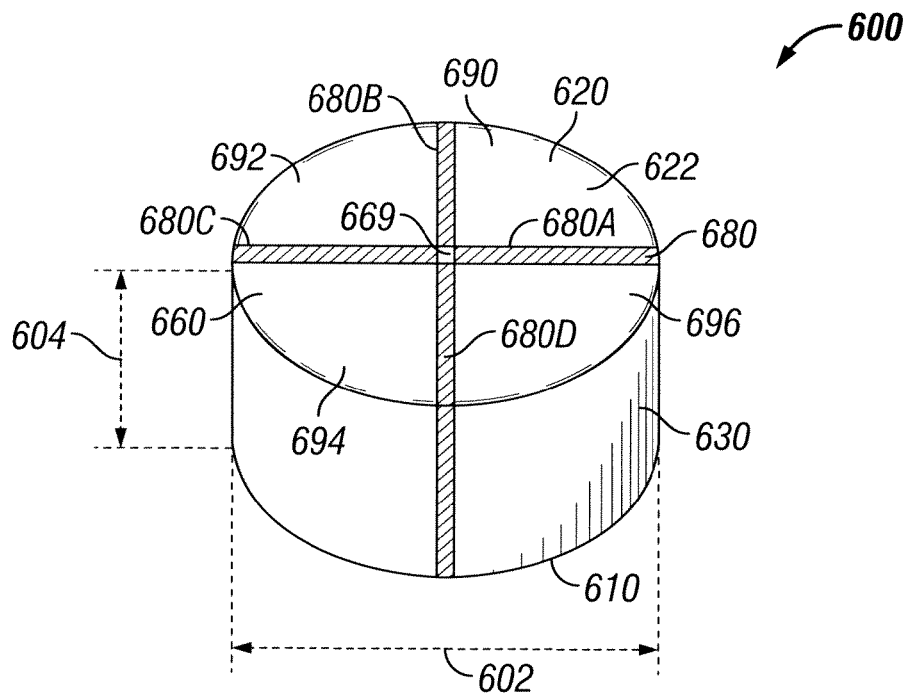
FIG. 6 shows a top perspective view of a target cylinder in accordance with an alternative exemplary embodiment of the invention.

FIG. 6 shows a top perspective view of a target cylinder 600 in accordance with an alternative exemplary embodiment of the invention. Referring to FIG. 6, the target cylinder 600 is cylindrically shaped and includes a first end 610, a second end 620, and a sidewall 630 extending from the first end 610 to the second end 620. According to this exemplary embodiment, the second end 620 is also referred to as an exposed portion 622 of the target cylinder 600 because the second end 620 is subjected to contact with the superhard component 100 (FIG. 1) when the testing is performed. The exposed portion 622 is substantially planar. Although the target cylinder 600 is cylindrically shaped, the target cylinder 600 can be any other geometric or non-geometric shape without departing from the scope and spirit of the exemplary embodiment. The target cylinder 600 has a diameter 602 of approximately three feet and a height 604 of approximately four inches. However, in alternate exemplary embodiments, the diameter 602 and/or the height 604 can vary according to the description provided above without departing from the scope and spirit of the exemplary embodiment. For example, the target cylinder 600 can be dimensioned and shaped to be used in the conventional granite log test also.

The target cylinder 600 is fabricated using a first material 660 and a second material 680 that is positioned in a predetermined pattern along the exposed portion 622, wherein the second material 680 is adjacent to and intervening within the first material 660, and wherein the first material 660 is a synthetic material similar to synthetic material 440 (FIG. 4). The synthetic first material 660 is formed from any of the materials and processes described above. According to some exemplary embodiments, the second material 680 is a natural rock type, such as granite. According to other exemplary embodiments, the second material 680 also is a synthetic material similar to synthetic material 440 (FIG. 4). In certain exemplary embodiments, the second material 680 is the same as first material 660. In some of the exemplary embodiments where the first material 660 is different than the second material 680, the first material 660 is either more or less abrasive than the second material 680 depending upon user desires. In some of the exemplary embodiments where the first material 660 is different than the second material 680, the first material 660 has either a higher or lower unconfined compressive strength than the second material 680 depending upon user desires. In some of the exemplary embodiments where the first material 660 is different than the second material 680, the first material 660 has either a higher or lower concentration of iron and/or iron alloys than the second material 680 depending upon user desires.

The fabrication of the target cylinder 600 is repeatable so that an initially formed target cylinder 600 is substantially similar to a subsequently formed target cylinder 600. The predetermined pattern for the second material 680 is repeatable so that the test results can be compared between tests conducted over time. According to FIG. 6, the second material 680 is a granite slab that is about ¾ inches, or about twenty millimeters, wide and extends from the exposed portion 622 to the first end 610. Although this exemplary embodiment uses a granite slab that is about ¾ inches, or about twenty millimeters, the width of the slabs can vary from about ⅕ inches, or about five millimeters, to about twelve inches in other exemplary embodiments or can also vary in width from one slab to another without departing from the scope and spirit of the exemplary embodiment. Additionally, although the second material 680 is shaped in substantially rectangular slabs, the second material 680 can be shaped in any other geometric or non-geometric shape without departing from the scope and spirit of the exemplary embodiment. Examples of the second material 680 include, but are not limited to, sandstone, limestone, marble, granite, wood, plastic, epoxy, synthetic materials described above, concrete, and other materials known to people having ordinary skill in the art. In alternative exemplary embodiments, the second material 680 can extend from the exposed portion 622 to a distance that is at least a portion of the height 604 without departing form the scope and spirit of the exemplary embodiment. In this exemplary embodiment, there are four pieces of second material 680A, 680B, 680C, and 680D, where each of the second materials 680A, 680B, 680C, and 680D are oriented to divide the exposed portion 622 into a first quadrant 690, a second quadrant 692, a third quadrant 694, and a fourth quadrant 696. Hence, the second material 680 is positioned in an "X-like" pattern.

Specifically, second material 680A is positioned at substantially ninety degrees to second material 680D and second material 680B. Second material 680B is positioned at substantially ninety degrees to second material 680A and second material 680C. Second material 680C is positioned at substantially ninety degrees to second material 680B and second material 680D. Second material 680D is positioned at substantially ninety degrees to second material 680C and second material 680A. Thus, four equally sized quadrants 690, 692, 694, and 696 are formed; however, the angles between the second materials 680A, 680B, 680C, and 680D can be varied so at least one quadrant is sized differently that the other quadrants. Although four quadrants 690, 692, 694, and 696 are formed at the exposed portion 622, greater or fewer quadrants can be formed at the exposed portion 622 by using more or less second material 680 slabs positioned interveningly between the first material 660 without departing from the scope and spirit of the exemplary embodiment. Optionally, the second material 680 can be oriented in a manner where a first material core 669 is formed at substantially the center of the target cylinder 600. Although not illustrated, alternatively, the second material 680 can be oriented in a manner where second material 680 also is positioned at substantially the center of the target cylinder 600.

The first material 660 forms the first quadrant 690, the second quadrant 692, the third quadrant 694, and the fourth quadrant 696. The first material 660 is any synthetic material having one or more properties of any one of compressive strength, abrasiveness, and/or iron content as previously mentioned with respect to FIG. 4. The first material 660 optionally can have additives included therein so long that the desired property requirements are still achieved. According to this exemplary embodiment, the first material 660 also extends from the exposed portion 622 to the first end 610.

In one exemplary embodiment, the difference of unconfined compressive strength between the second material 680 and the first material 660 ranges from about 1,000 psi to about 60,000 psi. In other exemplary embodiments, the difference of unconfined compressive strength between the second material 680 and the first material 660 ranges from about 4,000 psi to about 60,000 psi. In other exemplary embodiments, the difference of unconfined compressive strength between the second material 680 and the first material 660 ranges from about 6,000 psi to about 60,000 psi. In other exemplary embodiments, the difference of unconfined compressive strength between the second material 680 and the first material 660 ranges from about 10,000 psi to about 60,000 psi. In other exemplary embodiments, the difference of unconfined compressive strength between the second material 680 and the first material 660 ranges from about 15,000 psi to about 60,000 psi.

In this exemplary embodiment, second materials 680A, 680B, 680C, and 680D are fabricated from the same type of second material 680. However, according to certain alternative exemplary embodiments, one or more of second materials 680A, 680B, 680C, and 680D can be made from a different types of second materials 680, such as granite and marble slabs. Thus, each of second materials 680A, 680B, 680C, and 680D can be made from a different type of second material 680 or one or more of second materials 680A, 680B, 680C, and 680D can be made from the same type of second material 680 without departing from the scope and spirit of the exemplary embodiment.

Similarly, in this exemplary embodiment, each of the first quadrant 690, the second quadrant 692, the third quadrant 694, and the fourth quadrant 696 are formed from the same type of first material 660. However, according to certain alternative exemplary embodiments, one or more of the first quadrant 690, the second quadrant 692, the third quadrant 694, and the fourth quadrant 696 can be made from a different type of first material 660. Thus, each of the first quadrant 690, the second quadrant 692, the third quadrant 694, and the fourth quadrant 696 can be made from a different type of first material 660 or one or more of the first quadrant 690, the second quadrant 692, the third quadrant 694, and the fourth quadrant 696 can be made from the same type of first material 660 without departing from the scope and spirit of the exemplary embodiment.

The surface area of the target cylinder's exposed portion 622 is a combination of the first material 660 and the second material 680. In one exemplary embodiment, the percentage range of first material 660 is about five percent to about ten percent, while the percentage range of second material 680 is about ninety percent to about ninety-five percent. In another exemplary embodiment, the percentage range of first material 660 is about ten percent to about twenty-five percent, while the percentage range of second material 680 is about seventy-five percent to about ninety percent. In another exemplary embodiment, the percentage range of first material 660 is about twenty percent to about thirty-five percent, while the percentage range of second material 680 is about sixty-five percent to about eighty percent. In another exemplary embodiment, the percentage range of first material 660 is about thirty percent to about forty-five percent, while the percentage range of second material 680 is about fifty-five percent to about seventy percent. In another exemplary embodiment, the percentage range of first material 660 is about forty percent to about fifty-five percent, while the percentage range of second material 680 is about forty-five percent to about sixty percent. In another exemplary embodiment, the percentage range of first material 660 is about fifty percent to about sixty-five percent, while the percentage range of second material 680 is about thirty-five percent to about fifty percent. In another exemplary embodiment, the percentage range of first material 660 is about sixty percent to about seventy-five percent, while the percentage range of second material 680 is about twenty-five percent to about forty percent. In another exemplary embodiment, the percentage range of first material 660 is about seventy percent to about eighty-five percent, while the percentage range of second material 680 is about fifteen percent to about thirty percent. In another exemplary embodiment, the percentage range of first material 660 is about eighty percent to about ninety percent, while the percentage range of second material 680 is about ten percent to about twenty percent. In another exemplary embodiment, the percentage range of first material 660 is about ninety percent to about ninety-five percent, while the percentage range of second material 680 is about five percent to about ten percent.

Referring to FIGS. 5 and 6, the target cylinder 600 is formed by obtaining the casting form 500 and positioning the second material 680 upright within the casting form 500 in a predetermined pattern. According to one exemplary embodiment, the casting form 500 is cylindrical; however, the casting form 500 can be any other geometric or non-geometric shape. The casting form 500 is filled with the aggregate material 510 and the cementing agent 520 so that the resulting mixture 530 surrounds at least a portion of the second material 680. The mixture 530 is processed and hardened, thereby forming the first material 660, which surrounds at least a portion of the second material 680. Once hardened, the casting form 500 is removed and the exposed portion 622 is made smooth and substantially planar. The second material 680 is pre-fabricated according to some exemplary embodiments, regardless of whether the second material 680 is a natural material or a synthetic material. In other exemplary embodiments, the second material 680 is fabricated at the same time as the first material 660; for instance, when the second material 680 also is a synthetic material.

In some exemplary embodiments, an epoxy (not shown), such as Sikadur BTP®, is placed, or coated, onto the outer surfaces of the second material 680 which is to be bonded to the first material 660. The epoxy is a two-part epoxy according to some exemplary embodiments. The two-part epoxy includes a glue and a catalyst. Once the epoxy is coated onto the second material 680, the second material 680 is positioned within the casting form 500 according to the positions described above. The first material 660 is placed into the casting form 500 to surround the second material 680 and the epoxy. As the epoxy cures, the epoxy bonds to both the second material 680 and the first material 660, thereby effectively bonding the second material 680 to the first material 660. According to some exemplary embodiments, the epoxy cures in about fourteen days, however, other epoxies having longer or shorter cure times can be used in other exemplary embodiments. Upon the target cylinder 600 being cured and formed, the epoxy has a thickness ranging from about two millimeters to about fifteen millimeters; however, this thickness can be greater or less in other exemplary embodiments.

Alternatively, the target cylinder 600 is formed by obtaining a casting form 500 and filling it with the mixture 530, which includes the aggregate material 510 and the cementing agent 520. According to one exemplary embodiment, the casting form 500 is cylindrical; however, the casting form 500 can be any other geometric or non-geometric shape. The mixture 530 is processed, thereby forming the first material 660. The first material 660 is then slotted or drilled in a predetermined pattern to accept the second material 680 therein. The second material 680 is inserted upright into the slots and bonded to the first material 660 using a bonding material known to people having ordinary skill in the art, such as cement or an epoxy. The casting form 500 is removed and the exposed portion 622 is made smooth and substantially planar.

Once target cylinder 600 is formed, the target cylinder 600 can be used in the VBM test as described above. The target cylinder's first end 610 is coupled to the rotating table 310 (FIG. 3), thereby positioning the exposed portion 622 adjacent the tool holder 320 (FIG. 3) that has the cutter 100 (FIG. 3) mounted therein. Upon performing the VBM test using target cylinder 600, the abrasive wear resistance and/or the impact resistance for the PDC cutter 100 (FIG. 3) can be determined. During the test, the cutter 100 (FIG. 3) repeatedly makes transitions between higher compressive strength material and lower compressive strength material. According to one example where the first material 660 has a higher compressive strength than the second material 680, each time the cutter 100 (FIG. 3) engages the end of one of the first material 660, a front impact load is imparted to the cutting table 120 (FIG. 1) and substrate 110 (FIG. 1) as it passes across the first material 660. When the cutter 100 (FIG. 3) exits first material 660 and enters the second material 680, the compressive stress on the cutting table 120 is unloaded or released, thereby creating a rebound test of the substrate 110 (FIG. 1) to the cutting table 120 (FIG. 1) at the contact face 115 (FIG. 1) and hereby allows measurement of impact resistance.

Referring back to FIG. 6, the abrasive wear resistance is determined as a wear ratio, which is defined as the volume of target cylinder 600 that is removed to the volume of the PDC cutter 100 (FIG. 3) that is removed. Alternatively, instead of measuring volume, the distance that the PDC cutter 100 (FIG. 3) travels across the target cylinder 600 can be measured and used to quantify the abrasive wear resistance for the PDC cutter 100 (FIG. 3). Alternatively, other methods known to persons having ordinary skill in the art can be used to determine the wear resistance using the VBM test. Impact resistance for the PDC cutter 100 (FIG. 3) also can be determined using the same test by measuring the volume of diamond removed from the PDC cutter 100 (FIG. 3) through chipage. Alternatively, the impact resistance for the PDC cutter 100 (FIG. 3) can be determined by measuring the weight of diamond removed from the PDC cutter 100 (FIG. 3) through chipage. Alternatively, other methods known to persons having ordinary skill in the art can be used to determine the impact resistance using the VBM test.

The target cylinder 600 is able to test for both abrasive wear resistance and impact robustness of cutters 100 (FIG. 1) with a minimum consumption of time, target material, and test cutters. The target cylinder 600 can be made according to the same construction each time giving the test repeatability and continuity over the testing of numerous different cutter types. According to some exemplary embodiments, the target cylinder 600 is entirely made from first material 660. In other exemplary embodiments, the second material 680 is interveningly positioned at predetermined locations within the first material 660. The formulation of the first material 660 is maintained over time to ensure the test results are comparative over time. Although one predetermined pattern for having the second material 680 be interveningly positioned within the first material 660 is illustrated with respect to FIG. 6, the second material 680 can be interveningly positioned within the first material 660 in any repeatable predetermined patterns, some of which are illustrated with respect to FIGS. 7-9.

Figure 7:
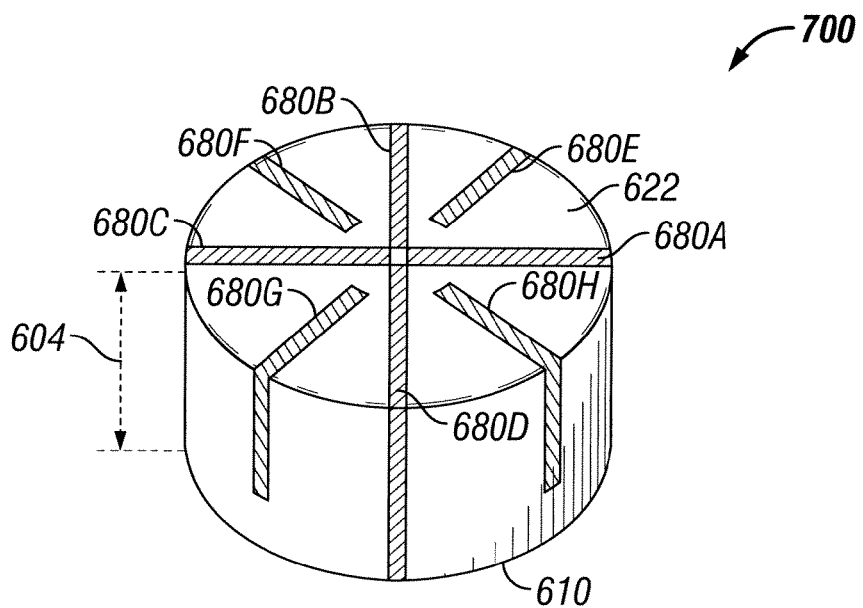
FIG. 7 shows a top perspective view of a target cylinder in accordance with a second alternative exemplary embodiment of the invention.

FIG. 7 shows a top perspective view of a target cylinder 700 in accordance with a second alternative exemplary embodiment of the invention. Target cylinder 700 is similar to target cylinder 600 except that additional second material 680E, 680F, 680G, and 680H are positioned within the target cylinder 700 and extend from the exposed portion 622 to a portion of the height 604. The exposed portion 622 is substantially planar. Second material 680E is positioned between second materials 680A and 680B so that it substantially bisects the angle formed between second materials 680A and 680B. Similarly, second material 680F is positioned between second materials 680B and 680C so that it substantially bisects the angle formed between second materials 680B and 680C. Similarly, second material 680G is positioned between second materials 680C and 680D so that it substantially bisects the angle formed between second materials 680C and 680D. Also, second material 680H is positioned between second materials 680D and 680A so that it substantially bisects the angle formed between second materials 680D and 680A. Hence, second materials 680 are positioned in a "spoke-like" pattern. Although additional second material 680E, 680F, 680G, and 680H extends from the exposed portion 622 to a distance that is a portion of the height 604, at least one of additional second material 680E, 680F, 680G, and 680H can extend from the exposed portion 622 to the first end 610 without departing from the scope and spirit of the exemplary embodiment. The alternative exemplary embodiments presented with respect to target cylinder 600 also apply to target cylinder 700. For example, one or more of the second materials 680A, 680B, 680C, 680D, 680E, 680F, 680G, and 680H can be made of different types of second materials 680. The target cylinder 700 is fabricated according to the processes described with respect to target cylinder 600 (FIG. 6).

Figure 8:
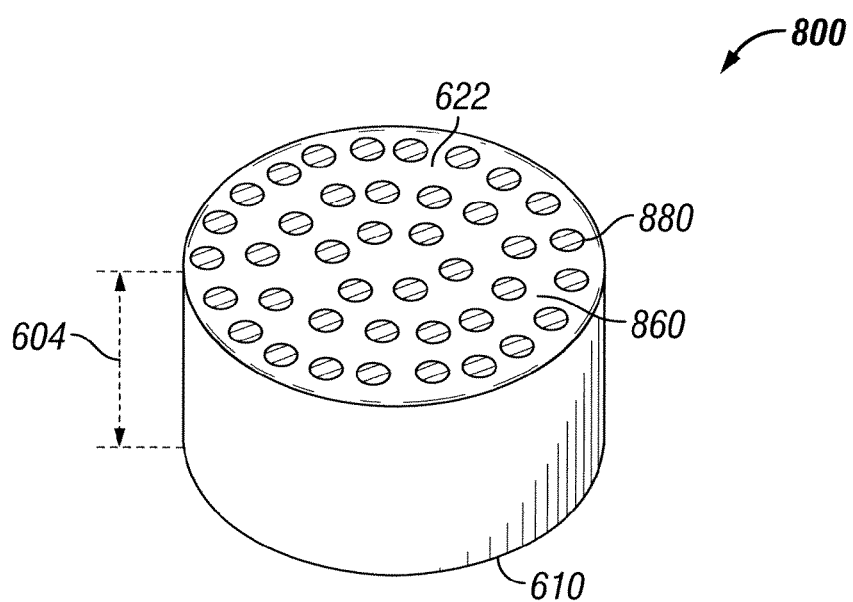
FIG. 8 shows a top perspective view of a target cylinder in accordance with a third alternative exemplary embodiment of the invention.

FIG. 8 shows a top perspective view of a target cylinder 800 in accordance with a third alternative exemplary embodiment of the invention. Target cylinder 800 is similar to target cylinder 600 (FIG. 6) except that the shape and positioning of the second material 880 is different than the shape and positioning of the second material 680A, 680BF, 680C, and 680D (FIG. 6). Referring to FIG. 8, the target cylinder 800 includes a first material 860 and a second material 880 that is positioned in a predetermined pattern along the exposed portion 622, wherein the second material 880 is adjacent to and intervening within the first material 860. The fabrication of the target cylinder 800 is repeatable so that an initially formed target cylinder 800 is substantially similar to a subsequently formed target cylinder 800. The predetermined pattern for the second material 880 is repeatable so that the test results can be compared between tests conducted over time. The first material 860 is similar to the first material 660 (FIG. 6). Similarly, second material 880 is similar to the second material 680 (FIG. 6). According to FIG. 8, the second material 880 is a cylindrical column that extends from the exposed portion 622 to the first end 610. In this exemplary embodiment, forty second materials 880 are positioned within the target cylinder 800 in a predetermined pattern and are surrounded by the first material 860. However, greater or fewer second materials 880 can be used without departing from the scope and spirit of the exemplary embodiment. According to some alternative exemplary embodiments, the second material 880 extends from the exposed portion 622 to a portion of the height 604 without departing form the scope and spirit of the exemplary embodiment. In using this target cylinder 800, the PDC cutters 100 (FIG. 3) are subjected to glancing blows against the second material 880. The alternative exemplary embodiments presented with respect to target cylinder 600 (FIG. 6) also apply to target cylinder 800. For example, one or more of the second materials 880 can be made of different types of second materials 880. The target cylinder 800 is fabricated according to the processes described with respect to target cylinder 600 (FIG. 6).

Figure 9:
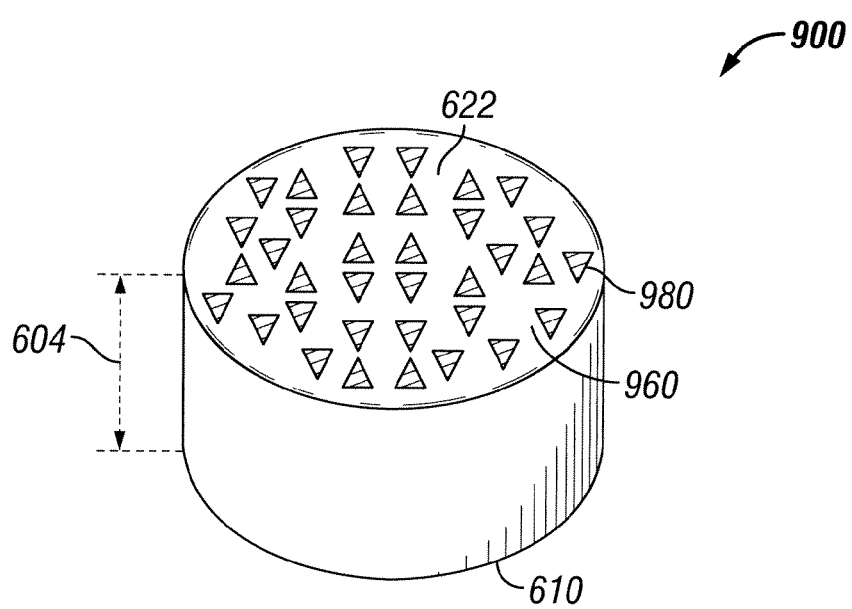
FIG. 9 shows a top perspective view of a target cylinder in accordance with a fourth alternative exemplary embodiment of the invention.

FIG. 9 shows a top perspective view of a target cylinder 900 in accordance with a fourth alternative exemplary embodiment of the invention. Target cylinder 900 is similar to target cylinder 800 (FIG. 8) except that the shape and positioning of the second material 980 is different than the shape and positioning of the second material 880 (FIG. 8). Referring to FIG. 9, the target cylinder 900 includes a first material 960 and a second material 980 that is positioned in a predetermined pattern along the exposed portion 622, wherein the second material 980 is adjacent to and intervening within the first material 960. The fabrication of the target cylinder 900 is repeatable so that an initially formed target cylinder 900 is substantially similar to a subsequently formed target cylinder 900. The first material 960 is similar to the first material 660 (FIG. 6). Similarly, second material 980 is similar to the second material 680 (FIG. 6). According to FIG. 9, the second material 980 is a triangular column that extends from the exposed portion 622 to the first end 610. In this exemplary embodiment, thirty-three second materials 980 are positioned within the target cylinder 900 in a predetermined pattern and are surrounded by the first material 960. However, greater or fewer second materials 980 can be used without departing from the scope and spirit of the exemplary embodiment. According to some alternative exemplary embodiments, the second material 980 extends from the exposed portion 622 to a portion of the height 604 without departing form the scope and spirit of the exemplary embodiment. The alternative exemplary embodiments presented with respect to target cylinder 600 (FIG. 6) also apply to target cylinder 900. For example, one or more of the second materials 980 can be made of different types of second materials 980. The target cylinder 900 is fabricated according to the processes described with respect to target cylinder 600 (FIG. 6).

Figure 10:
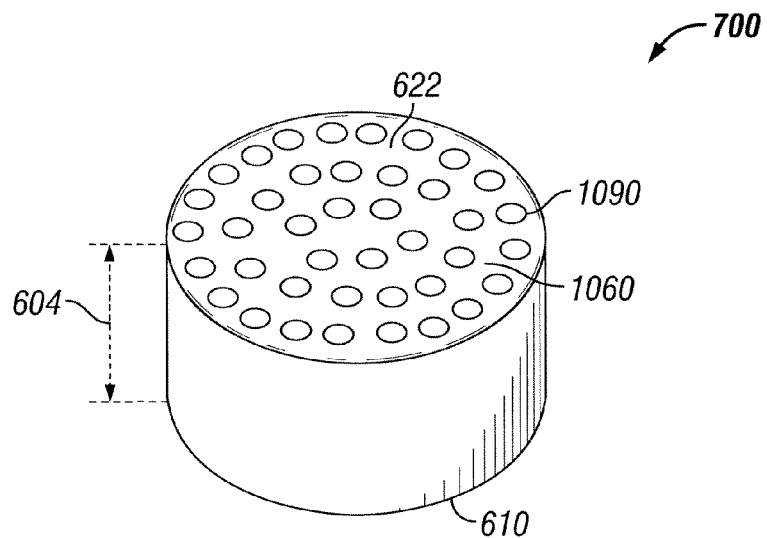
FIG. 10 shows a side perspective view of a target cylinder in accordance with a fifth alternative exemplary embodiment of the invention.

FIG. 10 shows a side perspective view of a target cylinder 1000 in accordance with a fifth alternative exemplary embodiment of the invention. Target cylinder 1000 is similar to target cylinder 600 (FIG. 6) except that openings or slots 1090 are formed at the surface of the exposed portion 622. The openings or slots 1090 are void of any material. Referring to FIG. 10, the target cylinder 1000 includes a first material 1060 and one or more openings or slots 1090 positioned in a predetermined pattern along the exposed portion 622, wherein the openings or slots 1090 are adjacent to and intervening within the first material 1060. The fabrication of the target cylinder 1000 is repeatable so that an initially formed target cylinder 1000 is substantially similar to a subsequently formed target cylinder 1000. The first material 1060 is similar to the first material 660 (FIG. 6). According to FIG. 10, the opening or slot 1090 is a circular cylindrical opening that extends from the exposed portion 622 to the first end 610. In this exemplary embodiment, forty openings or slots 1090 are positioned within the target cylinder 1000 in a predetermined pattern and are surrounded by the first material 1060. However, greater or fewer openings or slots 1090 can be used without departing from the scope and spirit of the exemplary embodiment. According to some alternative exemplary embodiments, the openings or slots 1090 extend from the exposed portion 622 to a distance that is a portion of the height 604 without departing form the scope and spirit of the exemplary embodiment. According to some exemplary embodiments, the shape of the openings or slots 1090 can be varied without departing from the scope and spirit of the exemplary embodiments. For example, the second material for any of the previously described embodiments can be replaced with an opening or slot 1090. In using this target cylinder 1000, the PDC cutters 100 (FIG. 3) are subjected to glancing blows against the openings or slots 1090 rather than against the second material 980 (FIG. 9). The openings or slots 1090 are formed after the first material 1060 is formed. According to one example, once the processing of the aggregate material 510 (FIG. 5) and the cementing agent 520 (FIG. 5) is completed and the first material 1060 is formed, the opening or slots 1090 are formed via drilling. The alternative exemplary embodiments presented with respect to target cylinder 600 (FIG. 6) also apply to target cylinder 1000.

Figure 11:
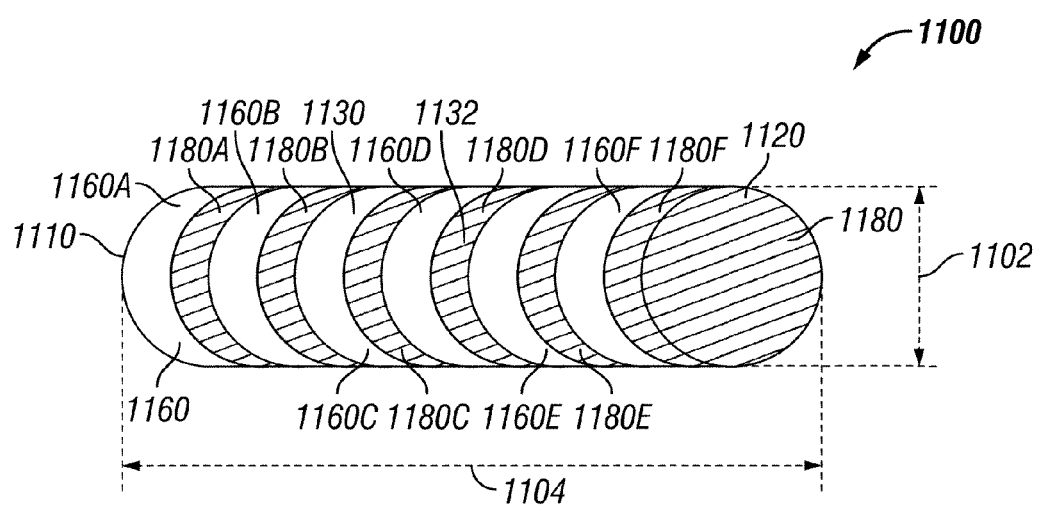
FIG. 11 shows a side perspective view of a target cylinder in accordance with a sixth alternative exemplary embodiment of the invention.

FIG. 11 shows a side perspective view of a target cylinder 1100 in accordance with a sixth alternative exemplary embodiment of the invention. Referring to FIG. 11, the target cylinder 1100 is a cylindrically shaped log and includes a first end 1110, a second end 1120, and a sidewall 1130 extending from the first end 1110 to the second end 1120. According to this exemplary embodiment, the sidewall 1130 is also referred to as an exposed portion 1132 of the target cylinder 1100 because the sidewall 1130 is subjected to contact with the superhard component 100 (FIG. 1) when the testing is performed. The target cylinder 1100 has a diameter 1102 of approximately six inches and a height 1104 of approximately two feet. However, in alternate exemplary embodiments, the diameter 1102 can range from about four inches to about six feet without departing from the scope and spirit of the exemplary embodiment. Additionally, in alternate exemplary embodiments, the height 1104 can range from about one inch to about twenty feet without departing from the scope and spirit of the exemplary embodiment.

The target cylinder 1100 includes a first material 1160 and a second material 1180 that is positioned in a predetermined pattern along the exposed portion 1132, where the second material 1180 is adjacent to the first material 1160. The fabrication of the target cylinder 1100 is repeatable so that an initially formed target cylinder 1100 is substantially similar to a subsequently formed target cylinder 1100. The predetermined pattern for the second material 1180 is repeatable so that the test results can be compared between tests conducted over time. According to FIG. 11, the second material 1180 is a granite band that is about two inches wide and has an outer diameter equal to the target cylinder's diameter 1102. Although this exemplary embodiment uses a granite band that is two inches wide for the second material 1180, the width of the band can vary from about one-half inch to about twelve inches in other exemplary embodiments or can also vary in width from one band to another without departing from the scope and spirit of the exemplary embodiment. Second material 1180 is similar to second material 680 (FIG. 6), as previously described, and can be fabricated from other natural rock types or synthetic materials as previously described.

The first material 1160 is a synthetic material band that is about two inches wide and has a outer diameter equal to the target cylinder's diameter 1102. Although this exemplary embodiment uses a synthetic material band that is two inches wide, the width of the band can vary from about one-half inch to about twelve inches in other exemplary embodiments or can also vary in width from one band to another without departing from the scope and spirit of the exemplary embodiment. First material 1160 is similar to first material 660 (FIG. 6), as previously described.

According to FIG. 11, target cylinder 1100 is formed using six first materials 1160A, 1160B, 1160C, 1160D, 1160E, and 1160F and six second materials 1180A, 1180B, 1180C, 1180D, 1180E, and 1180F. The second materials 1180A, 1180B, 1180C, 1180D, 1180E, and 1180F are coupled to the first materials 1160A, 1160B, 1160C, 1160D, 1160E, and 1160F in an alternating manner. In this exemplary embodiment, second materials 1180A, 1180B, 1180C, 1180D, 1180E, and 1180F are fabricated from the same material. However, according to certain alternative exemplary embodiments, one or more of second materials 1180A, 1180B, 1180C, 1180D, 1180E, and 1180F can be made from a different type of second material. Thus, each of second materials 1180A, 1180B, 1180C, 1180D, 1180E, and 1180F can be made from a different type of second material or one or more of second materials 1180A, 1180B, 1180C, 1180D, 1180E, and 1180F can be made from the same type of second material without departing from the scope and spirit of the exemplary embodiment.

Similarly, in this exemplary embodiment, first materials 1160A, 1160B, 1160C, 1160D, 1160E, and 1160F are fabricated from the same material. However, according to certain alternative exemplary embodiments, one or more of first materials 1160A, 1160B, 1160C, 1160D, 1160E, and 1160F can be made from a different type of first material. Thus, each of first materials 1160A, 1160B, 1160C, 1160D, 1160E, and 1160F can be made from a different type of first material or one or more of first materials 1160A, 1160B, 1160C, 1160D, 1160E, and 1160F can be made from the same type of first material without departing from the scope and spirit of the exemplary embodiment.

The surface area of the target cylinder's 1100 exposed portion 1132 is a combination of the first material 1160 and the second material 1180. In one exemplary embodiment, the percentage range of first material 1160 is about five percent to about ten percent, while the percentage range of second material 1180 is about ninety percent to about ninety-five percent. In another exemplary embodiment, the percentage range of first material 1160 is about ten percent to about twenty-five percent, while the percentage range of second material 1180 is about seventy-five percent to about ninety percent. In another exemplary embodiment, the percentage range of first material 1160 is about twenty percent to about thirty-five percent, while the percentage range of first material 1180 is about sixty-five percent to about eighty percent. In another exemplary embodiment, the percentage range of first material 1160 is about thirty percent to about forty-five percent, while the percentage range of second material 1180 is about fifty-five percent to about seventy percent. In another exemplary embodiment, the percentage range of first material 1160 is about forty percent to about fifty-five percent, while the percentage range of second material 1180 is about forty-five percent to about sixty percent. In another exemplary embodiment, the percentage range of first material 1160 is about fifty percent to about sixty-five percent, while the percentage range of second material 1180 is about thirty-five percent to about fifty percent. In another exemplary embodiment, the percentage range of first material 1160 is about sixty percent to about seventy-five percent, while the percentage range of second material 1180 is about twenty-five percent to about forty percent. In another exemplary embodiment, the percentage range of first material 1160 is about seventy percent to about eighty-five percent, while the percentage range of second material 1180 is about fifteen percent to about thirty percent. In another exemplary embodiment, the percentage range of first material 1160 is about eighty percent to about ninety percent, while the percentage range of second material 1180 is about ten percent to about twenty percent. In another exemplary embodiment, the percentage range of first material 1160 is about ninety percent to about ninety-five percent, while the percentage range of second material 1180 is about five percent to about ten percent.

The target cylinder 1100 is formed by obtaining a casting form (not shown) and loading the casting form from bottom to top with alternating bands of first material 1160 and second material 1180. Each time the first material 1160 is loaded into the casting form, the first material 1160 is allowed to cool and harden before loading the second material 1180 above the first material 1160. According to one exemplary embodiment, the casting form is cylindrical. Once the desired number of bands are formed and the desired height of the target cylinder 1100 is formed, the casting form is removed and the exposed portion 1132 is smoothened.

In some exemplary embodiments, an epoxy (not shown), such as Sikadur BTP®, is placed, or coated, onto the outer surface of either or both the second material 1180 and the first material 1160 prior to the second material 1180 being loaded on top of the first material 1160. The epoxy is a two-part epoxy according to some exemplary embodiments. The two-part epoxy includes a glue and a catalyst. As the epoxy cures, the epoxy bonds to both the second material 1180 and the first material 1160, thereby effectively bonding the second material 1180 to the first material 1160. According to some exemplary embodiments, the epoxy cures in about fourteen days, however, other epoxies having longer or shorter cure times can be used in other exemplary embodiments. Upon the target cylinder 1100 being cured and formed, the epoxy has a thickness ranging from about two millimeters to about fifteen millimeters; however, this thickness can be greater or less in other exemplary embodiments.

Once target cylinder 1100 is formed, the target cylinder 1100 can be used in the granite log test as described above. The target cylinder's first end 1110 is coupled to the chuck 210 (FIG. 2) and the second end 1120 is coupled to the tailstock 220 (FIG. 2), thereby positioning the exposed portion 1132 adjacent the tool post 230 (FIG. 2) that has the cutter 100 (FIG. 2) mounted therein. Upon performing the granite log test using target cylinder 1100, the abrasive wear resistance and/or the impact resistance for the PDC cutter 100 (FIG. 2) can be determined. During the test, the cutter 100 (FIG. 2) repeatedly makes transitions between the first material 1160 and the second material 1180, wherein one of the first or second materials has a higher compressive strength than the other material. In the example where the first material 1160 has the higher compressive strength than the second material 1180, each time the cutter 100 (FIG. 2) engages the end of one of the first material 1160, a front impact load is imparted to the cutting table 120 (FIG. 1) and substrate 110 (FIG. 1) as it passes across the first material 1160. When the cutter 100 (FIG. 2) exits first material 1160 and enters the second material 1180, the compressive stress on the cutting table 120 (FIG. 1) is unloaded or released, thereby creating a rebound test of the substrate 110 (FIG. 1) to the cutting table 120 (FIG. 1) at the contact face 115 (FIG. 1).

Figure 2:
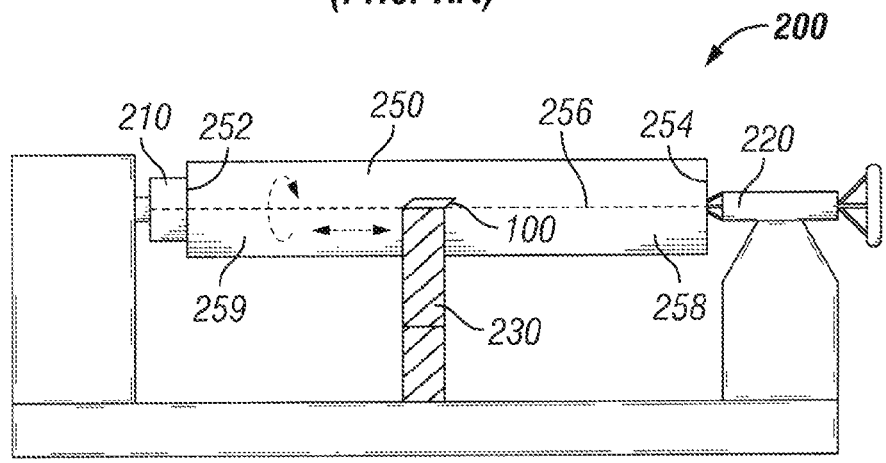
FIG. 2 shows a lathe for testing abrasive wear resistance of a superhard component using a conventional granite log test.

The abrasive wear resistance is determined as a wear ratio, which is defined as the volume of target cylinder 1100 that is removed to the volume of the PDC cutter 100 (FIG. 2) that is removed. Alternatively, instead of measuring volume, the distance that the PDC cutter 100 (FIG. 2) travels across the target cylinder 1100 can be measured and used to quantify the abrasive wear resistance for the PDC cutter 100 (FIG. 2). Alternatively, other methods known to persons having ordinary skill in the art can be used to determine the wear resistance using the granite log test. Impact resistance for the PDC cutter 100 (FIG. 2) also can be determined using the same test by measuring the volume of rock removed from the PDC cutter 100 (FIG. 2) through chipage. Alternatively, the impact resistance for the PDC cutter 100 (FIG. 2) can be determined by measuring the weight of rock removed from the PDC cutter 100 (FIG. 2) through chipage. Alternatively, other methods known to persons having ordinary skill in the art can be used to determine the impact resistance using the granite log test.

The target cylinder 1100 is able to test for both abrasive wear resistance and impact robustness of cutters 100 (FIG. 1) with a minimum consumption of time, target material, and test cutters. The target cylinder 1100 can be made according to the same construction each time giving the test repeatability and continuity over the testing of numerous different cutter types. According to some exemplary embodiments, the target cylinder 1100 is entirely made from first material 1160. The formulation of the first material 1160 and second material 1180 is maintained over time to ensure the test results are comparative over time.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

What is claimed is:

1. A target cylinder, comprising:
a first end
a second end; and
a sidewall extending from the first end to the second end, wherein at least one of the first end, the second end, or the sidewall is an exposed portion, the exposed portion being fabricated using at least one synthetic material, the synthetic material comprising a first unconfined compressive strength ranging from 12 kpsi to 30 kpsi, wherein the exposed portion makes contact with a superhard component to facilitate determination of at least one property of the superhard component.

2. The target cylinder of claim 1, wherein the first unconfined compressive strength ranges from 15 kpsi to 25 kpsi.

3. The target cylinder of claim 1, wherein the synthetic material comprises an abrasiveness ranging from 1 Cerchars to 6 Cerchars.

4. The target cylinder of claim 1, wherein the synthetic material comprises an abrasiveness ranging from 3 Cerchars to 6 Cerchars.

5. The target cylinder of claim 1, wherein the synthetic material comprises an iron content ranging from 5 percent to 10 percent.

6. The target cylinder of claim 1, wherein the synthetic material comprises at least one aggregate material and at least one cementing agent.

7. The target cylinder of claim 6, wherein the aggregate material is selected from at least one of a blast media or a foundry casting media.

8. The target cylinder of claim 6, wherein the cementing agent is selected from at least one of sodium silicate, a plastic resin, a multi-part epoxy resin, clay based ceramic particles, or an abrasive cement.

9. The target cylinder of claim 6, wherein the aggregate material and the cementing agent are bonded together using at least one of vitrified bonds, resinoid bonds, silicate bonds, shellac bonds, rubber bonds, or oxychloride bonds.

10. The target cylinder of claim 1, wherein the exposed portion further comprises one or more second materials positioned interveningly within the synthetic material in a predetermined and repeatable pattern.

11. The target cylinder of claim 10, wherein the second material is selected from at least one of a second synthetic material, a natural rock type, or wood.

12. The target cylinder of claim 10, wherein the second material comprises a second unconfined compressive strength, and wherein the differential between the second unconfined compressive strength and the first unconfined compressive strength ranges from 1,000 psi to 60,000 psi.

13. The target cylinder of claim 10, wherein the synthetic material comprises a percent composition of the target cylinder that is greater than or equal to the percent composition of the second material.

14. The target cylinder of claim 10, wherein at least one of the second materials comprises a different unconfined compressive strength than the remaining second materials.

15. The target cylinder of claim 10, wherein the second material is bonded to the synthetic material using an epoxy.

16. The target cylinder of claim 15, wherein the epoxy comprises a two-part epoxy.

17. The target cylinder of claim 15, wherein the epoxy comprises a thickness ranging from 2 millimeters to 15 millimeters once the epoxy has cured.

18. The target cylinder of claim 1, wherein at least one of the synthetic materials comprises a different unconfined compressive strength than the remaining synthetic materials.

19. The target cylinder of claim 1, wherein when the second end or the first end is the exposed portion, the target cylinder is coupled to a vertical boring mill.

20. The target cylinder of claim 1, wherein when the sidewall is the exposed portion, the target cylinder is coupled to a lathe.

21. The target cylinder of claim 1, wherein the synthetic material forms one or more openings at the surface of the exposed portion, the openings being positioned interveningly within the synthetic material in a predetermined and repeatable pattern.

22. The target cylinder of claim 1, wherein the target cylinder is shaped into a wheel, the wheel being coupled to a grinding wheel.

23. A method for testing a superhard component on a target cylinder, comprising:
 obtaining a superhard component;
 obtaining a target cylinder, wherein the target cylinder comprises:
  a first end;
  a second end; and
  a sidewall extending, from the first end to the second end,
  wherein at least one of the first end, the second end, or the sidewall is an exposed portion, the exposed portion being fabricated using at least one synthetic material, the synthetic material comprising a first unconfined compressive strength ranging from about 12 kpsi to 30 kpsi;
 contacting the superhard component with the exposed portion of the target cylinder;
 allowing the superhard component to move across the exposed portion; and
 determining at least one property of the superhard component.

24. The method of claim 23, wherein the synthetic material comprises an abrasiveness ranging from 1 Cerchars to 6 Cerchars.

25. The method of claim 23, wherein the synthetic material comprises an iron content ranging from 5 percent to 10 percent.

26. The method of claim 23, wherein the exposed portion further, comprises one or more second materials positioned interveningly within the synthetic material in a predetermined and repeatable pattern.

27. The method of claim 26, wherein the second material is selected from at least one of a second synthetic material, a natural rock type, or wood.

28. The method of claim 26, wherein the second material comprises a second unconfined compressive strength, and wherein the differential between the second unconfined compressive strength and the first unconfined compressive strength ranges from 1,000 psi to 60,000 psi.

29. The method of claim 26, wherein the synthetic material comprises a percent composition of the target cylinder that is greater than or equal to the percent composition of the second material.

30. The method of claim 26, wherein at least one of the second materials comprises a different unconfined compressive strength than the remaining second materials.

31. The target cylinder of claim 26, wherein the second material is bonded to the synthetic material using an epoxy.

32. The method of claim 23, wherein at least one of the synthetic materials comprises a different unconfined compressive strength than the remaining synthetic materials.

33. The method of claim 23, wherein the synthetic material forms one or more openings at the surface of the exposed portion, the openings being positioned interveningly within the synthetic material in a predetermined and repeatable pattern.

34. The method of claim 23, wherein the step for determining at least one property of the superhard component comprises determining the abrasiveness of the superhard component and determining the impact resistance of the superhard component.

* * * * *